United States Patent
Boddy et al.

(10) Patent No.: US 12,247,966 B2
(45) Date of Patent: Mar. 11, 2025

(54) SYSTEM AND METHOD FOR AUTOMATED PHENOTYPING OF SHATTERED SEED PODS

(71) Applicant: Monsanto Technology LLC, St. Louis, MO (US)

(72) Inventors: Kelly Boddy, St. Louis, MO (US); Dale Burns, St. Louis, MO (US); Brian Forinash, St. Louis, MO (US); Martin Gaudet, St. Louis, MO (US); Alan Jackson, St. Louis, MO (US); Graham McGregor, St. Louis, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 264 days.

(21) Appl. No.: 17/924,181

(22) PCT Filed: Jan. 12, 2021

(86) PCT No.: PCT/US2021/013096
§ 371 (c)(1),
(2) Date: Nov. 9, 2022

(87) PCT Pub. No.: WO2021/230923
PCT Pub. Date: Nov. 18, 2021

(65) Prior Publication Data
US 2023/0176025 A1  Jun. 8, 2023

Related U.S. Application Data
(60) Provisional application No. 63/023,269, filed on May 12, 2020.

(51) Int. Cl.
*G01N 33/00* (2006.01)
*G01V 8/14* (2006.01)

(52) U.S. Cl.
CPC ........... *G01N 33/0098* (2013.01); *G01V 8/14* (2013.01)

(58) Field of Classification Search
CPC .......................... G06V 20/188; G05D 1/0246
See application file for complete search history.

(56) References Cited

U.S. PATENT DOCUMENTS 3,786,941 A * 1/1974 Dailey, Jr. .............. A01D 45/16
414/508
6,449,932 B1 * 9/2002 Cooper .................. G01N 21/85
56/10.2 R (Continued)

FOREIGN PATENT DOCUMENTS

CN  202886247 U  4/2013
WO  2016046418 A1  3/2016

OTHER PUBLICATIONS

Romkaew Jutamas et al: "Pod Dehiscence in Soybean : Assessing Methods and Varietal Difference," Plant Production Science, vol. 9, No. 4, Dec. 3, 2015 (Dec. 3, 2015) pp. 373-382, XP093129402, ISSN: 1342-943X, DOI: 10. 1626/pps.9.373; URL:https://dx.doi.org/10.1626/pps.9.373.

(Continued)

*Primary Examiner* — Tran M. Tran
(74) *Attorney, Agent, or Firm* — Sandberg Phoenix & von Gontard, P.C.

(57) ABSTRACT

A seed pod shatter test system for determining the resistance to seed pod shattering in various plants, wherein the system comprises a mobile platform that is structured and operable to traverse at least one row of plants growing in plot, and at least one plant engaging head mounted to a front of the mobile platform. The at least one plant engaging head is structured and operable to condition each of the plurality of plants by contacting each of the plants in the row(s) with a predetermined amount of force as the mobile platform (Continued)

traverse the row(s) of plants. The system additionally comprises a data collections and analysis system that is structured and operable to determine an amount of seed pod shattering that occurred in the plurality of plants as a result of the conditioning.

20 Claims, 8 Drawing Sheets

(56) References Cited

U.S. PATENT DOCUMENTS

| | | | | |
|---|---|---|---|---|
| 7,600,642 | B2* | 10/2009 | Deppermann | G01N 35/02 209/552 |
| 7,765,780 | B2* | 8/2010 | Koselka | A01D 46/30 701/50 |
| 8,008,541 | B2* | 8/2011 | Anstrom | C12N 15/8209 800/300 |
| 8,479,482 | B2* | 7/2013 | Moreira | A01D 45/00 56/14.6 |
| 8,608,439 | B2* | 12/2013 | Hill | F04D 19/002 416/37 |
| 8,809,635 | B2 | 8/2014 | Laga et al. | |
| 9,392,743 | B2* | 7/2016 | Camacho-Cook | A01B 69/008 |
| 9,658,201 | B2* | 5/2017 | Redden | A01C 21/007 |
| 10,178,828 | B2* | 1/2019 | Hendrickson | G01N 33/0098 |
| 10,568,316 | B2* | 2/2020 | Gall | G01N 21/4738 |
| 10,845,810 | B2* | 11/2020 | Flajolet | G06T 7/579 |
| 10,890,912 | B2* | 1/2021 | Cavender-Bares | A01C 7/00 |
| 11,215,597 | B2* | 1/2022 | Overton | G01M 5/0091 |
| 11,357,189 | B2* | 6/2022 | Laga | C12N 15/8266 |
| 11,758,845 | B2* | 9/2023 | Zielke | G01B 5/10 340/425.1 |
| 11,789,453 | B2* | 10/2023 | Chowdhary | G06T 7/155 382/110 |
| 12,025,602 | B2* | 7/2024 | Shore | B64U 30/20 |
| 12,055,522 | B2* | 8/2024 | Marzu | G01N 33/0098 |
| 12,063,885 | B2* | 8/2024 | Meyers | A01D 41/1273 |
| 12,094,199 | B2* | 9/2024 | Chowdhary | G06V 20/56 |
| 12,119,086 | B2* | 10/2024 | Bauer | C12Q 1/6895 |
| 2002/0004418 | A1 | 1/2002 | Mesquita et al. | |
| 2009/0293440 | A1 | 12/2009 | Moreira et al. | |
| 2013/0263562 | A1* | 10/2013 | Moreira | A01D 45/00 56/130 |
| 2013/0263563 | A1* | 10/2013 | Moreira | A01D 45/22 56/14.7 |
| 2015/0027040 | A1 | 1/2015 | Redden | |
| 2017/0169314 | A1* | 6/2017 | Dijkman | G06F 18/2163 |

OTHER PUBLICATIONS

International Search Report for PCT/US2021/013096 mailed Mar. 25, 2021.
Written Opinion for PCT/US2021/013096 mailed Mar. 25, 2021.

\* cited by examiner

TABLE 1: PSH RATINGS BASED ON PERCENTAGE OF PODS SHATTERED

| PSH RATING | APPROXIMATE % OF PODS SHATTERED |
|---|---|
| 1 | 10% – NO SEED LOSS |
| 2 | 20% |
| 3 | 30% |
| 4 | 40% |
| 5 | 50% |
| 6 | 60% |
| 7 | 70% |
| 8 | 80% |
| 9 | 90% – COMPLETE SHATTERING/SEED LOSS |

FIG. 8

SYSTEM AND METHOD FOR AUTOMATED PHENOTYPING OF SHATTERED SEED PODS

CROSS-REFERENCE TO RELATED APPLICATIONS

The present application is the US national stage under 35 U.S.C. § 371 of International Application No. PCT/US2021/013096 which was filed on Jan. 12, 2021, and which claims the priority of U.S. Provisional Application No. 63/023,269, filed on May 12, 2020. The disclosures of the above applications are incorporated herein by reference in their entirety.

FIELD

The present teachings relate to crop seed pod shattering prior to harvest, and more specifically to systems and methods to test the resistance to seed pod shattering of various crops.

BACKGROUND

The statements in this section merely provide background information related to the present disclosure and may not constitute prior art.

For growers of various plants that have seed pods, for example crucifiers, legumes and flowers such as canola, wheat, peas, radish, poppy, various oil seeds plants such as soybeans, cotton, sunflower, peanuts, etc., seed pod shattering is a concern because it reduces final harvest. Plant seed pod shattering occurs when the seed pods break open and release their seeds prematurely, e.g. before or during the process of harvest, resulting in the seed being lost and a reduced yield. Growers want plants that do not shatter (i.e. shatter resistant). There is ongoing research investigating ways to produce plants that are resistant to seed pod shattering. However, seed pod shattering is a very difficult genetic trait to measure, and current methods of detecting and quantifying shatter resistant phenotypes are slow, subjective, and inefficient.

The present disclosure provides high-throughput systems and methods of objectively phenotyping crops by generating data that accurately represent the tendency of the seed pods of a plant and/or group of plants to shatter. For example, in various embodiments, the present disclosure provides a mobile seed pod shatter test system that is structured and operable to contact fertilized plants of a crop or plot to simulate environmental conditions and elements, such as wind, rain and hail that can cause undesired pod shattering. In certain embodiments, the seed pod shatter test system comprises at least one plant engaging head mounted to a mobile platform. Each plant engaging head comprises a rotating spindle having a plurality of plant contact members mounted thereto. The seed pod shatter test system additionally includes a data collection system capable of collecting information about the plants conditioned, or processed, by the seed pod shatter test system, whereby the collected information can be utilized to make decisions in a plant breeding pipeline. For example, the data collection system can measure the amount of pod shattering caused in one or more plants by the pod shatter test system to determine whether the plant(s) should be used as a parent in future commercial plant products. In certain embodiments the data collected is in the form of electromagnetic radiation emitted or reflected from a plant that can be associated with the amount of shattering in the plant, i.e. a shattering phenotype.

In various embodiments, the present disclosure provides a seed pod shatter test system for determining the resistance to seed pod shattering in various plants, wherein the system comprises a mobile platform that is structured and operable to traverse at least one row of plants growing in plot, and at least one plant engaging head mounted to a front of the mobile platform. The at least one plant engaging head is structured and operable to condition each of the plurality of plants by contacting each of the plants in the row(s) with a predetermined amount of force as the mobile platform traverse the row(s) of plants. The system additionally comprises a data collections and analysis system that is structured and operable to determine an amount of seed pod shattering that occurred in the plurality of plants as a result of the conditioning.

This summary is provided merely for purposes of summarizing various example embodiments of the present disclosure so as to provide a basic understanding of various aspects of the teachings herein. Various embodiments, aspects, and advantages will become apparent from the following detailed description taken in conjunction with the accompanying drawings which illustrate, by way of example, the principles of the described embodiments. Accordingly, it should be understood that the description and specific examples set forth herein are intended for purposes of illustration only and are not intended to limit the scope of the present teachings.

DRAWINGS

The drawings described herein are for illustration purposes only and are not intended to limit the scope of the present teachings in any way.

Corresponding reference numerals indicate corresponding parts throughout the several views of drawings.

DETAILED DESCRIPTION

The following description is merely exemplary in nature and is in no way intended to limit the present teachings, application, or uses. Throughout this specification, like reference numerals will be used to refer to like elements. Additionally, the embodiments disclosed below are not intended to be exhaustive or to limit the invention to the precise forms disclosed in the following detailed description. Rather, the embodiments are chosen and described so that others skilled in the art can utilize their teachings. As well, it should be understood that the drawings are intended to illustrate and plainly disclose presently envisioned embodiments to one of skill in the art, but are not intended to be manufacturing level drawings or renditions of final products and may include simplified conceptual views to facilitate understanding or explanation. As well, the relative size and arrangement of the components may differ from that shown and still operate within the spirit of the invention.

As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims.

Unless otherwise defined, all technical and scientific terms used herein have the same meaning as commonly understood by one of ordinary skill in the art to which this disclosure belongs. The terminology used herein is for the purpose of describing particular example embodiments only and is not intended to be limiting. As used herein, the singular forms "a", "an", and "the" may be intended to include the plural forms as well, unless the context clearly indicates otherwise. The terms "comprises", "comprising", "including", and "having" are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps can be employed.

When an element, object, device, apparatus, component, region or section, etc., is referred to as being "on", "engaged to or with", "connected to or with", or "coupled to or with" another element, object, device, apparatus, component, region or section, etc., it can be directly on, engaged, connected or coupled to or with the other element, object, device, apparatus, component, region or section, etc., or intervening elements, objects, devices, apparatuses, components, regions or sections, etc., can be present. In contrast, when an element, object, device, apparatus, component, region or section, etc., is referred to as being "directly on", "directly engaged to", "directly connected to", or "directly coupled to" another element, object, device, apparatus, component, region or section, etc., there may be no intervening elements, objects, devices, apparatuses, components, regions or sections, etc., present. Other words used to describe the relationship between elements, objects, devices, apparatuses, components, regions or sections, etc., should be interpreted in a like fashion (e.g., "between" versus "directly between", "adjacent" versus "directly adjacent", etc.).

As used herein the phrase "operably connected to" will be understood to mean two are more elements, objects, devices, apparatuses, components, etc., that are directly or indirectly connected to each other in an operational and/or cooperative manner such that operation or function of at least one of the elements, objects, devices, apparatuses, components, etc., imparts are causes operation or function of at least one other of the elements, objects, devices, apparatuses, components, etc. Such imparting or causing of operation or function can be unilateral or bilateral.

As used herein, the term "and/or" includes any and all combinations of one or more of the associated listed items. For example, A and/or B includes A alone, or B alone, or both A and B.

Although the terms first, second, third, etc. can be used herein to describe various elements, objects, devices, apparatuses, components, regions or sections, etc., these elements, objects, devices, apparatuses, components, regions or sections, etc., should not be limited by these terms. These terms may be used only to distinguish one element, object, device, apparatus, component, region or section, etc., from another element, object, device, apparatus, component, region or section, etc., and do not necessarily imply a sequence or order unless clearly indicated by the context.

Moreover, it will be understood that various directions such as "upper", "lower", "bottom", "top", "left", "right", "first", "second" and so forth are made only with respect to explanation in conjunction with the drawings, and that components may be oriented differently, for instance, during transportation and manufacturing as well as operation. Because many varying and different embodiments may be made within the scope of the concept(s) taught herein, and because many modifications may be made in the embodiments described herein, it is to be understood that the details herein are to be interpreted as illustrative and non-limiting.

The apparatuses/systems and methods described herein can be implemented at least in part by one or more computer program products comprising one or more non-transitory, tangible, computer-readable mediums storing computer programs with instructions that may be performed by one or more processors. The computer programs may include processor executable instructions and/or instructions that may be translated or otherwise interpreted by a processor such that the processor may perform the instructions. The computer programs can also include stored data. Non-limiting examples of the non-transitory, tangible, computer readable medium are nonvolatile memory, magnetic storage, and optical storage.

As used herein, the term module can refer to, be part of, or include an application specific integrated circuit (ASIC); an electronic circuit; a combinational logic circuit; a field programmable gate array (FPGA); a processor (shared, dedicated, or group) that performs instructions included in code, including for example, execution of executable code instructions and/or interpretation/translation of uncompiled code; other suitable hardware components that provide the described functionality; or a combination of some or all of the above, such as in a system-on-chip. The term module can include memory (shared, dedicated, or group) that stores code executed by the processor.

The term code, as used herein, can include software, firmware, and/or microcode, and can refer to one or more programs, routines, functions, classes, and/or objects. The term shared, as used herein, means that some or all code from multiple modules can be executed using a single (shared) processor. In addition, some or all code from multiple modules can be stored by a single (shared) memory. The term group, as used above, means that some or all code from a single module can be executed using a group of processors. In addition, some or all code from a single module can be stored using a group of memories.

As used herein, grain, seed or other plant product exemplarily includes oilseeds cereals and legumes such as wheat, corn, rye, soybeans, oats, rice, millet, canola, and any other seed or plant product collected from a plant, all of which are generically referred to herein simply as plant product. Additionally, as used herein, a test plot will be understood to mean a single field, or one of a plurality plots within a research field that has been subdivided into a plurality of plots. Each test plot typically comprises one or more rows of plants comprising from about 5 to about 15 or 20 plants (or more) in each row, wherein the plants are subject to various crop breeding and analytics research procedures and tests for developing various strains, hybrids, genotypes, etc. of plants. For example, test plots in a growing area can receive certain treatments (e.g. chemical applications to the plants and/or growing environment), and/or can comprise plants of certain genetics, and/or combinations thereof. Each test plot within a field can be purposely separated from other test plots by a gap, or alleys, where no plants are grown. The gaps or alleys maintain the identity of the plant material within each respective test plot. Hence, there are typically many alleys in a research field, often comprising 10-30 feet of space with no plants.

It should be noted that systems and methods disclosed herein are not limited to research and development scenarios and/or not limited to testing plants at testing locations and/or at locations where plots are separated by gaps, alleys, etc. In certain embodiments, the systems and methods disclosed herein can be used in commercial settings to determine plant performance on "plots" comprising dozens, hundreds, thousands or more plants of a certain type and/or plants subjected to certain growing conditions. For example, a grower may wish to compare the performance of plants growing in one environment (e.g. a certain soil type) to the performance of plants growing in a different environment (e.g. a different soil type) using this invention. Such cases would not require gaps or alleys in planting to prevent comingling of the values as a pre-defined "management zone" map and an accurate global positioning system (GPS) could be used to accurately associate plants growing in one environment verses another.

As used herein, a test plot will be understood to mean a single field, or one of a plurality plots within a research field that has been subdivided into a plurality of plots. Each test plot typically comprises one or more rows of plants comprising from about 5 to about 15 or 20 plants in each row, wherein the plants are subject to various crop breeding and analytics research procedures and tests for developing various strains, hybrids, genotypes, etc. of plants. For example, test plots in a growing area can receive certain treatments (e.g. chemical applications to the plants and/or growing environment), and/or can comprise plants of certain genetics, and/or combinations thereof. Each test plot within a field is purposely separated from other test plots by a gap, or alleys, where no plants are grown. The gaps or alleys maintain the identity of the plant material within each respective test plot. Hence, there are typically many alleys in a research field, often comprising 10-30 feet of space with no plants.

As used herein the term plant refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

As used herein the phrase population of plants or plant population means a set comprising any number, including one, of individuals, objects, or data from which samples are taken for evaluation, e.g. estimating QTL effects and/or disease tolerance. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but can also derive from two or more crosses between the same or different parents. Although a population of plants can comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

Referring to FIGS. 1, 2, 3 and 4, in various embodiments the present disclosure provides a high-throughput mobile seed pod shatter test system 10 (simply referred to herein as the shatter test system 10) that is structured and operable to contact fertilized plants 14 of a crop, field or plot 18 (exemplarily referred to herein as a test plot 18) to simulate environmental conditions and elements, such as wind, rain and hail, that can cause undesired pod shattering. More particularly, the shatter test system 10 provides a high-throughput system and methods for objectively phenotyping crops by generating data that accurately represent the tendency of the seed pods of one or more plants 14 to shatter.

The shatter test system 10 generally comprises a mobile platform 22, one or more plant engaging head(s) 26 mounted to the mobile platform 22, and a data collection and analysis system 30 that is wholly or partially mounted to the mobile platform 22 and/or wholly or partially remotely located. In various embodiments, the shatter test system 10 can comprise a plurality of the plant engaging heads 26, e.g., 2, 3, 4 or more, however, for simplicity and clarity, only a single plant engaging head 26 will be described herein. The mobile platform 22 is structured and operable to move through a test plot 18 comprising at least one row of plants having a plurality of plants 14 therein (e.g., 5-20 plants). The mobile platform 22 can be manually moved (e.g., pushed or pulled) through the test plot 18 or motorized to be propelled through the test plot 18 via a prime mover (e.g., an internal combustion engine, and/or an electric motor, etc.). When motorized, movement and control of the mobile platform 22 through the test plot 18 can be manually controlled and/or automatically controlled and/or remotely controlled. The data collection and analysis system 30 comprises a computer-based data processing system 34 communicatively (wired or wirelessly) to at least one plant imager 38.

The data processing system 34 can be wholly or partially located on the mobile platform 22, and the plant imager(s) 38 can be mounted to the mobile platform 22 and/or to an imager carrier 42 that is separate from the mobile platform 22, such as an unmanned aerial vehicle (e.g., a drone) or a separate terrestrial vehicle. The data collection and analysis system 30 is structured and operable to collect phenotypic and/or genotypic information about the plants 14 that have been conditioned, or processed by the shatter test system 10, whereby the collected information can be utilized to make decisions in a plant breeding pipeline. For example, the data collection and analysis system 30 can: 1) collect data indicative of the amount of pod shattering caused in one or more plants 14 by the shatter test system 10; and 2) process the collected data to determine whether the plant(s) 14 should be used as a parent in future commercial plant products. Each of the one or more plant engaging heads 26 comprises one or more plant contact implements 46 mounted to a motorized barrel 50 that is rotationally mounted with a head housing 56 and operably connected to, and rotationally driven by, a motor 52 (e.g., an electric motor and/or internal combustion engine) (shown in FIGS. 2 and 4). The motor 52 operationally connected to the barrel and structured and operable to controllably rotate the barrel about a longitudinal axis of the barrel 50.

As described in detail herein, the shatter test system 10 is structured and operable to move along the row(s) of a test plot 18 at a substantially consistent speed, whereby the rotating plant contact implement(s) 46 contact the plants 14 in one or more rows (e.g., 2, 3 or 4 rows) to move or jostle the plants 14 in a manner similar to the manner in which the plants 14 would be moved or jostled by various normal environmental conditions, such as wind, rain or hail. In various implementations, image data of the plants 14 is captured by the imager(s) 38 after the plants 14 have been engaged by the plant engaging head(s) 26 (e.g., contacted by the rotating plant contact implement(s) 46), whereafter it is analyzed by the data processing system 34 to determine an amount of pod shatter resulting therefrom. Alternatively, in various implementations, a first imager 38 can capture image data of the plants 14 prior to being engaged by the plant engaging head(s) 26, and then second imager 38 can capture image data of the plants 14 subsequent to being engaged by the plant engaging head(s) 26. The data processing system 34 can then compare image data collected prior to engagement by the plant engaging head(s) 26 to that collected subsequent to engagement by the plant engaging head(s) 26 to determine an amount of pod shatter resulting from the plants 14 being engaged by the plant engaging head(s) 26. As described above, the resulting pod shatter data can then be utilized to determine whether the plant(s) 14 in a particular row of a particular test plot 18 should be used as a parent in the breeding of future commercial plant products.

In various embodiments, the shatter test system 10 can further comprise a lift assembly 54 connected to the mobile platform 22 to which the plant engaging head(s) 26 is/are mounted. The lift assembly 54 is structured and operable to raise and lower the plant engaging head(s) 26, as described herein, such that the plant engaging head(s) 26 can be positioned at a desired height above the ground, and more particularly, below the tops or canopy of the plants 14 in the respective test plot 18. By setting the height of the plant engaging head(s) 26 at a selected height, the plant contact implement(s) 46 can strike or contact each plant 14 approximately at a desired location below the top of the respective plants 14 (e.g., 5-10 inches below the tops of the respective plants 14). The lift assembly 54 can be any assembly, mechanism or apparatus suitable for positioning and retaining the plant engaging head(s) 26 at the desired height as the shatter test system 10 traverse a respective test plot 18.

In various embodiments, the lift assembly 54 can comprise and automated actuator 60 communicatively connected (wired or wirelessly) to the data processing system 30. The automated actuator 60 is structured and operable to raise and lower the lift assembly 54 to automatically adjust the height of the plant engaging head(s) 26 for each plant 14 as the shatter test system 10 moves along the respective row(s) of plants 14 within the test plot 18 such that each respective plant 14 is more accurately contacted by the contact implement(s) 46 at the desired and selected distance below the top of the respective plants 14. Specifically, operation of the lift assembly 54 can be controlled by the computer based data processing system 34 (as are the operation of various other systems, mechanisms, assemblies, devices, etc. of the shatter test system 10) to raise or lower the plant engaging head(s) 26, in real time, based on the height of the next plant 14 (e.g., a target plant 14) in the respective row to be operated on (i.e., be contacted by the plant contact implement(s) 46), such that each respective plant 14 is contacted at the desired and selected distance below the top of the respective plant 14. The next plant 14 in the respective row to be operated on (i.e., be contacted by the plant contact implement(s) 46) will be referred to herein as the target plant 14. Hence, each plant 14 in a row of plants will momentarily be a target plant (i.e., the next plant to be operated on) as the shatter test system 10 moves along the respective row and traverses the respective test plot 18.

The data processing system 34, as described herein, can be any general-purpose computer comprising electronic memory (shared, dedicated or group), e.g., a hard drive, external flash drive, 'Cloud' based storage, or other electronic memory device, and a processor suitable for executing one or more plant analytics programs, algorithms, routines and/or other code (hereafter referred to simply as the plant analytics software) that can utilize various data such as height sensor data (described below), received location data (e.g., GPS data), received electronic instructions, and/or other captured data to raise and lower the plant engaging head(s) 26 (via the lift assembly 54), and/or record and analyze the data, and/or map the location of each plant, and/or make plant selection decisions, and/or determine any desired course of action and/or carry out such actions as the shatter test system 10 travels down or over the rows of plants 14. Alternatively, it is envisioned that the data processing system 34 can be any other computer based system or device disposed on the mobile platform 22 or remotely from the mobile platform 22 such as a smart phone, hand held computer, tablet or other computer based system/device that comprises memory and a processor capable of executing the plant analytics software. Additionally, it is envisioned that the data processing system 34 can comprise any combination of a general-purpose computer (as described above), any other computer based system or device (as described above), and one or more application specific integrated circuits (ASICs), electronic circuits, combinational logic circuits, field programmable gate arrays (FPGA), or other hardware components that provide various functionality of the shatter test system 10, as described herein.

Figure 4:
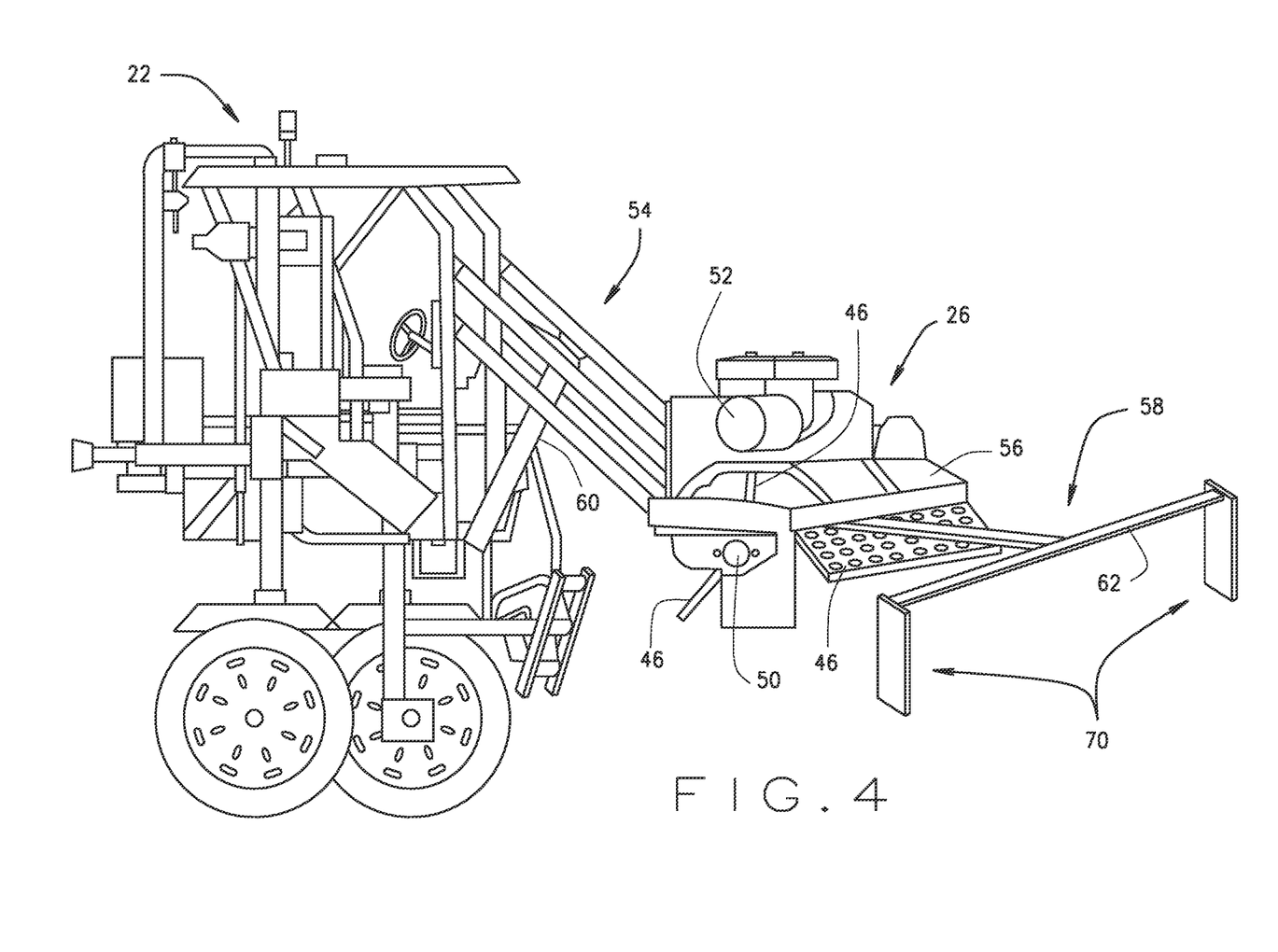
FIG. 4 is an isometric view of a front portion of the mobile seed pod shatter test system shown in FIGS. 1, 2 and 3 exemplarily illustrating a lift assembly sensor system, in accordance with various embodiments of the present disclosure.

Referring FIG. 4, in various embodiments operation of the lift assembly 54 can be controlled by the computer based data processing system 34 to raise or lower the plant engaging head(s) 26, in real time, based on the height of the next plant 14 (e.g., a target plant 14) in the respective row to be operated on such that each respective plant 14 is contacted at the desired and selected distance below the top of the respective plant 14. To accomplish the automated real time height adjustment of the plant engaging head(s) 26, in various embodiments, the shatter test system can include a sensor bar assembly 58 that is structured and operable to detect, and communicate to the data processing system 34, the presence and/or the location of the top of the target plant 14 (e.g., determine the height above the ground of the top of the target plant 12) in the respective row of plants 14 being operated on. In various implementations, the sensor bar 58 can be an angled sensor bar such as that described in issue U.S. Pat. No. 10,342,176, titled Angled Sensor Bar For Detecting Plants, issued Jul. 9, 2019 to the same assignee as the present application, the disclosure of which is incorporated herein by reference in its entirety. Subsequently, utilizing the information received from the sensor bar assembly 58, the data processing system 34 will control the lift assembly 54 to raise or lower the plant engaging head(s) 26 after operating on a present target plant 14, and prior to operating on a subsequent target plant 14, such that the top each respective plant 14 in the respective row is determined and the height of the plant engaging head(s) 26 adjusted so that the contact implement(s) 46 will contact each respective plant 14 approximately at the desired and selected distance below the top of the respective plant 14.

In various instances the sensor bar assembly 58 can include a sensor bar 62 mounted to or near a distal end of a sensor boom 66 and a sensor system 70 mounted at or near at least one of opposing ends of the sensor bar 62. The sensor boom 66 can be mounted to the lift assembly 54 and/or the plant engaging head(s) 26 such that that the sensor bar 62 and sensor system 70 are disposed a desired distance in front of the plant engaging head(s) 26. The sensor system 70 is structured and operable to detect the target plant 14 within a sensing field of the sensor system 70, and then detect the top of the target plant 14. The sensor system 70 can be any system capable of sensing the top of each plant 14 in the row(s) being conditioned as the shatter test system 10 moves along the respective row(s). For example, in various embodiments, the sensor system 70 can be an optical based system, a magnetic based system, a sonic based system, an image-based system, a tactile based system, etc. The sensing field of the sensor system 70 is defined herein to the area (having a length/range, width and height) in which the respective sensor system 70 is capable of sensing the presence of a plant 14 and the top of each respective plant 14.

In various embodiments, the sensor bar 62 can have a length such that the opposing ends will be positioned above lanes between adjacent rows of plants 14 when the shatter test system 10 is moved through the test plot 18, via the mobile platform 22, having the sensor boom 66 substantially aligned with the row of plants 14 being operated on. Lanes are defined herein as the longitudinal spaces between and parallel with adjacent rows of plants 14. More specifically, the sensor bar 62 has a length such that the sensor system 70, disposed on one or both ends of the sensor bar 62, is/are positioned within one or both adjacent lanes of the row of plants 14 being operated on. Accordingly, the sensor system 70 is/are positioned to be able to sense the presence and height of one or more plants 14 in front of the plant engaging head(s) 26 in the row of plants 14 being operated on. For example, in various embodiments, the sensor bar 62 can have a length between 42 inches and 66 inches, e.g., 54 inches Referring now to FIGS. 4 and 5, the sensor system 70 can comprise any system suitable for detecting the target plant 14 within a sensing field of the sensor system 70, and then detecting the top of the target plant 14. For example, in various embodiments, the sensor system 70 comprise at least one light emitting transceiver 74, e.g., at least one infrared (IR), or laser beam, transceiver, that is connected at a first end of the angled sensor bar 62, and at least one optical reflector 78 connected at an opposing second end of the angled sensor bar 62. The reflector(s) 78 can comprise any suitable reflective surface such as reflective tape, reflective plastic, a mirror, etc. In such embodiments, the length of the sensor bar 62 is such that, as the mobile platform 18 moves through the test plot 18, the transceiver(s) 74 is/are disposed within a first lane on a first side of a single row of plants 14 being operated on and the reflector(s) 78 is/are disposed within a second lane on an opposing second side of the single row of plants 14 being operated on. Thus, one or more of the plants 14 in the single row are within the sensing field between the transceiver(s) 74 and the reflector(s) 78. The sensing field is a line-of-sight, or area-of-sight, between the transceiver(s) 74 and the reflector(s) 78.

Figure 5:
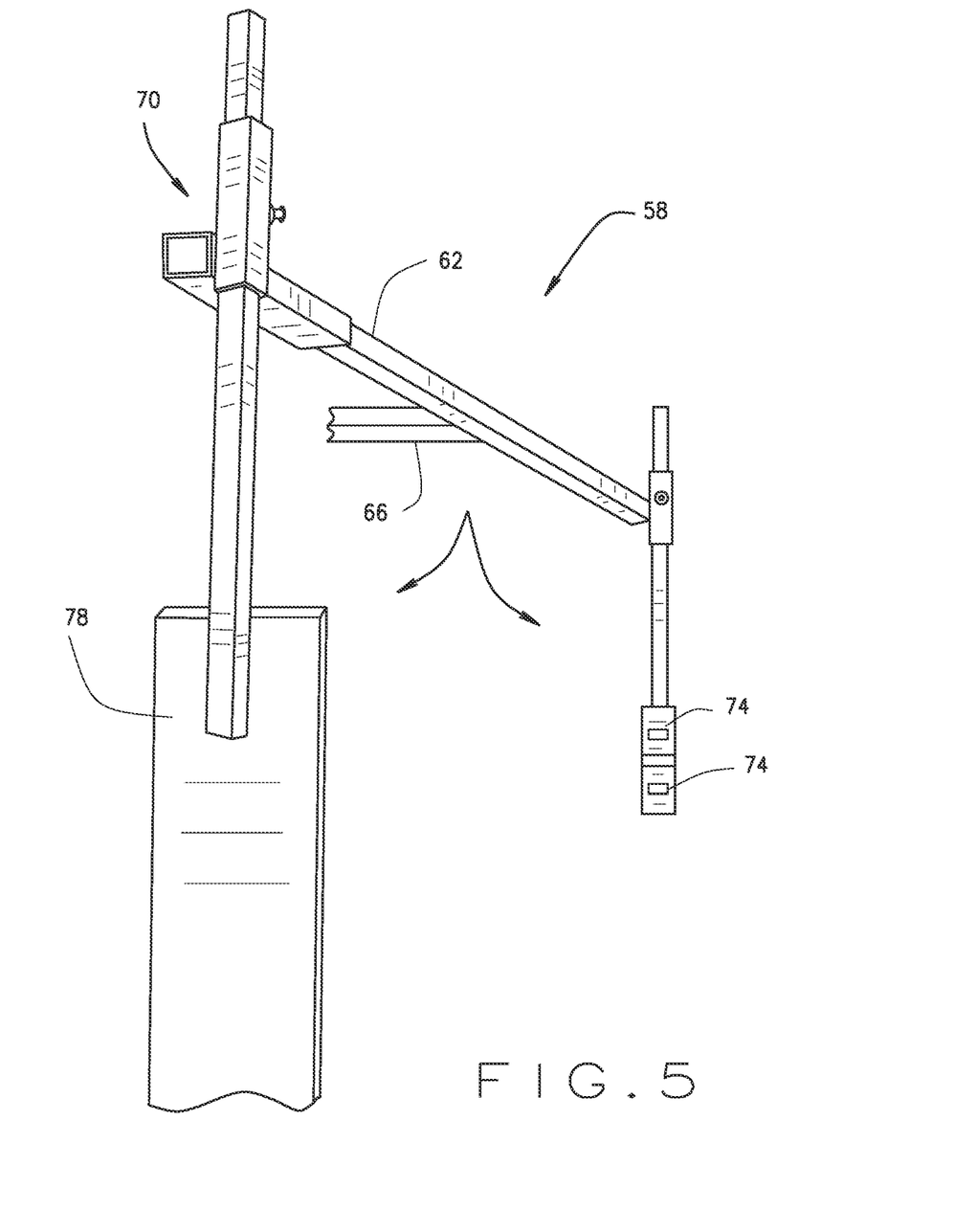
FIG. 5 is an exemplarily illustration of the lift assembly sensor system shown FIG. 4, in accordance with various embodiments of the present disclosure.

As described above, the transceiver(s) is/are communicatively connected (e.g., wired or wirelessly) to the data processing system 34. In such embodiments, each transceiver 74 can comprise an emitter that is structured and operable to emit beam of light toward the reflector(s) 78, and a receiver structured and operable to receive any portion of the emitted light reflected back from the reflector(s) 78. If reflected light is received, the transceiver(s) 74 communicate(s) to the data processing system 34 that there is no plant 14 present within the sensing field. If no reflected light is received, the transceiver(s) 74 communicate(s) to the data processing system 34 that there is at least one plant 14 present within the sensing field. If at least one plant 14 is sensed, the data processing system 34 can control raising the sensor bar assembly 58 and the plant engaging head(s) 26 until the reflected light is received indicating that transceiver(s) 74 have/has been raised to a height that is just above the top of the plant(s) 14 within the sensing field. Once the top of the plant(s) 14 is/are sensed, the data processing system 34 can raise or lower, via the lift assembly 54, the plant engaging head(s) 26 to approximately a desired distance below the top of the respective target plant 14 such that the plant contact implements will strike or contact the target plant 14 approximately at a desired location. Conversely, if no plant 14 is sensed within the sensing field, the data processing system 34 can control lowering the sensor bar assembly 58 and the plant engaging head(s) 26 until the reflected light is no longer received indicating that transceiver(s) 74 have/has been lowered to a height that is at the top of the plant(s) 14 within the sensing field. Once the top of the plant(s) 14 is/are sensed, the data processing system 34 can raise or lower, via the lift assembly 54, the plant engaging head(s) 26 to approximately a desired distance below the top of the respective target plant 14 such that the plant contact implements will strike or contact the target plant 14 approximately at a desired location.

Accordingly, in various implementations, as the shatter test system 10 travels through a test plot 18 along one or more rows of plants 14, the plant engaging head(s) 26 are moved up and/or down as needed to position the plant engaging head(s) 26 approximately at desired distance below the top of each respective target plant 14 such that the rotating plant contact implements will strike or contact the target plant 14 approximately at a location on the target plant 14 that will simulate jostling or moving the target plant 14 in a manner similar to the manner in which the target plant 14 would be moved or jostled by various environmental conditions, such as wind, rain or hail. The plant engaging head(s) 26 can be moved up and/or down via automation utilizing the sensor bar assembly 58, as exemplarily described above, or via motorization controlled by an operator of the shatter test system 10. Alternatively, in various other implementations, the height of the plant engaging head(s) 26 can be set to particular height based on the average height of the plants 14 in a test plot 18 and maintained at that height as the shatter test system 10 travels through the test plot 18 along one or more rows of plants 14.

Referring again to FIGS. 1, 2, 3 and 4, as described above, each of the one or more plant engaging heads 26 comprises one or more plant contact implements 46 (e.g., 1, 2, 3, 4 or more) mounted to the motorized barrel 50 that is operably connected to, and rotationally driven by, the motor 52 (e.g., an electric motor and/or internal combustion engine). In various embodiments, the motor can be communicatively connected (wired or wirelessly) to the data processing system 34, whereby the data processing system 34 can monitor and control in real time the speed and direction of rotation of the barrel 50, and hence the speed and direction of rotation of plant contact implement(s) 46. Accordingly, in various implementations, the speed and/or direction of rotation plant contact implement(s) 46 can be maintained at a constant speed and/or direction. Or, alternatively the speed and/or direction of rotation plant contact implement(s) 46 can be controllably varied in real time as the shatter test system 10 moves through the test plot 18.

More specifically, the force of contact between the plants 14 and the plant contact implement(s) 46 can be precisely adjusted to a predetermined force value by changing the rate at which the barrel 50 rotates. The seed pods of certain types plants 14 may shatter very easily, and thus require softer contact to induce shattering, while other types may require more forceful contact for the seed pods to shatter. Hence, in various embodiments, the rotational speed of the plant contact implement(s) 46 can be precisely controlled to create varying amounts of shattering in the plants 14 and/or among different plant types. Accordingly, in various embodiments, the rotational speed of the plant contact implement(s) 46 can be precisely controlled to create a consistent amount of seed pod shattering in a particular group plants 14 and/or among different plant types to compensate for changing other variables that affect shattering such as the terrestrial speed of the shatter test system 10 through the respective test plot 18.

For example, the rotational speed of the plant contact implement(s) 46 can be adjusted (e.g., monitored and changed) in real time based on the monitored terrestrial speed of shatter test system 10 such that a predetermined contact force at which the plant contact implement(s) 46 strike each plant 14 is substantially consistent. Generally, the contact force of the plant contact implement(s) 46 is equal to the linear velocity of the plant contact implement(s) 46 plus the linear velocity of the shatter test system 10. Controlling and adjusting the rotational speed of the plant contact implement(s) 46 in real time, based on the speed at which the shatter test system 10 is moving through the test plot 18, will thereby control in real time the contact force at which the plant contact implement(s) 46 strike each plant 14 subject each plant 14. More particularly, controlling in real time the contact force at which the plant contact implement(s) 46 strike each plant 14 will subject each plant 14 to substantially the same contact force, which will result in the production more consistent and reliable shatter resistance data.

It is envisioned that for each set of a plurality of test plots 18 in a particular location or field (each test plot 18 having a different type or hybrid plants 14) that are to have their seed pod resistance tested using the shatter test system 10 (i.e., for each trial), the respective trial is designed to be run with plant contact implement(s) 46 having a particular rotational speed that is used throughout the trial. More particularly, in various instances, the rotational speed of the plant contact implement(s) 46 for each trial is determined via a 'tolerant check', that is, by testing a tolerant hybrid versus a non-tolerant. This is done because the environmental conditions at each test site can be drastically different. For example, some test sites can be hot and dry, while others can be cool and damp. Hence, a 'tolerant check' can be performed at each test site to determine the proper rotational speed of the plant contact implement(s) 46.

Each plant engaging head barrel 50 and motor 52 are structured and operable to rotate the plant contact implement(s) 46 in either direction along an axis of the barrel 50. For example, as exemplarily shown in FIG. 1, in various implementations, the motor 52 can rotate the barrel 50 such that the plant contact implement(s) 46 contact each plant 14 with an upward contact motion. This is, such that the plant contact implement(s) 46 initially contacts each plant 14 at location lower on the plant 14 then travels up the plant 14 and separates from the plant 14 at a location higher on the plant than the initial contact. Alternatively, in various implementations, the motor 52 can rotate the barrel 50 such that the plant contact implement(s) 46 contact each plant 14 with a downward contact motion. This is, such that the plant contact implement(s) 46 initially contacts each plant at location higher on the plant 14 then travels down the plant 14 and separates from the plant 14 at a location lower on the plant than the initial contact. Empirical testing has shown that contacting the plant with an upward contact motion most closely simulates the movement or jostling that would occur in the plants 14 resulting from normal environmental conditions, such as wind, rain or hail. Additionally, the plant contact implement(s) 46 can comprise any item, apparatus, mechanism or system that is connectable to the plant engaging head barrel and suitable for contacting the plants 14 in a manner that simulates normal environmental conditions, such as wind, rain or hail. For example, empirical testing has shown that, when rotated at a predetermined speed, perforated mats similar to the ergonomic floor mats provided in restaurants, bars, industrial manufacturing plants, etc., for employees to stand on (to reduce foot and back strain), closely simulate the movement and jostling of the plants 14 that occurs under normal environmental conditions, such as wind, rain or hail.

Figure 1:
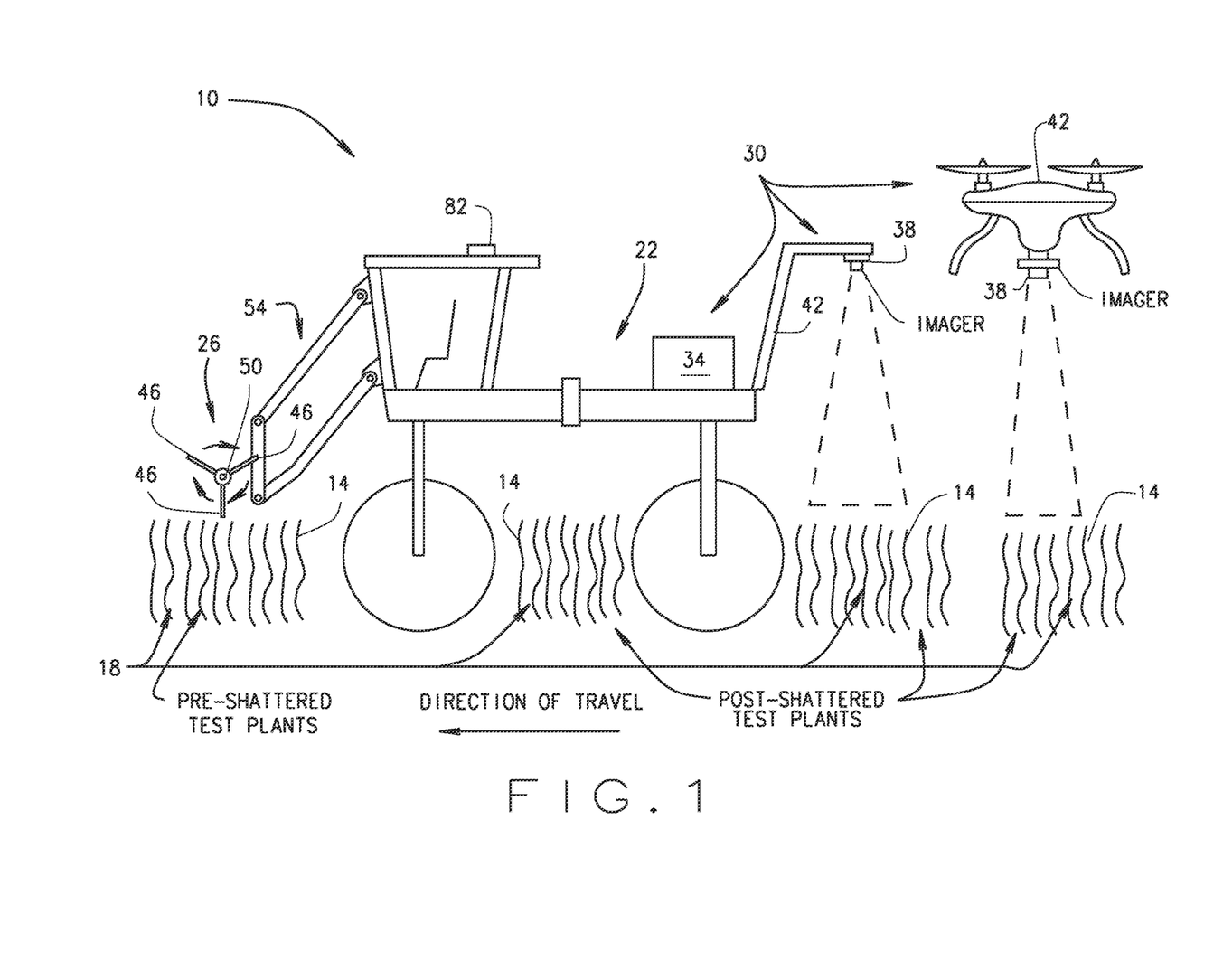
FIG. 1 is side view of a mobile seed pod shatter test system for determining a seed pod shatter resistance of a plurality plants in a test plot, in accordance with various embodiments of the present disclosure.
Figure 2:
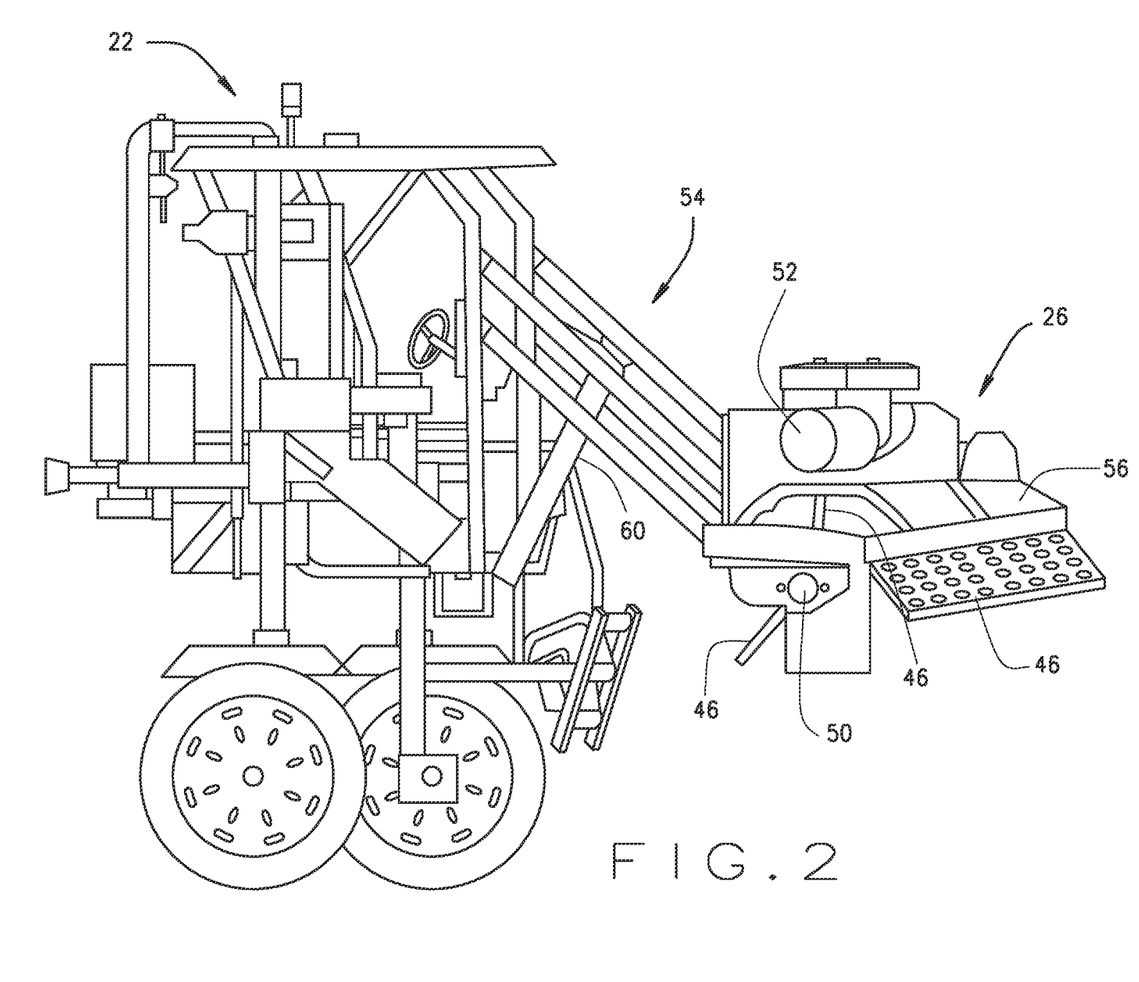
FIG. 2 is an isometric view of a front portion of the mobile seed pod shatter test system shown in FIG. 1 exemplarily illustrating a plant engaging head and lift assembly of the system, in accordance with various embodiments of the present disclosure.
Figure 3:
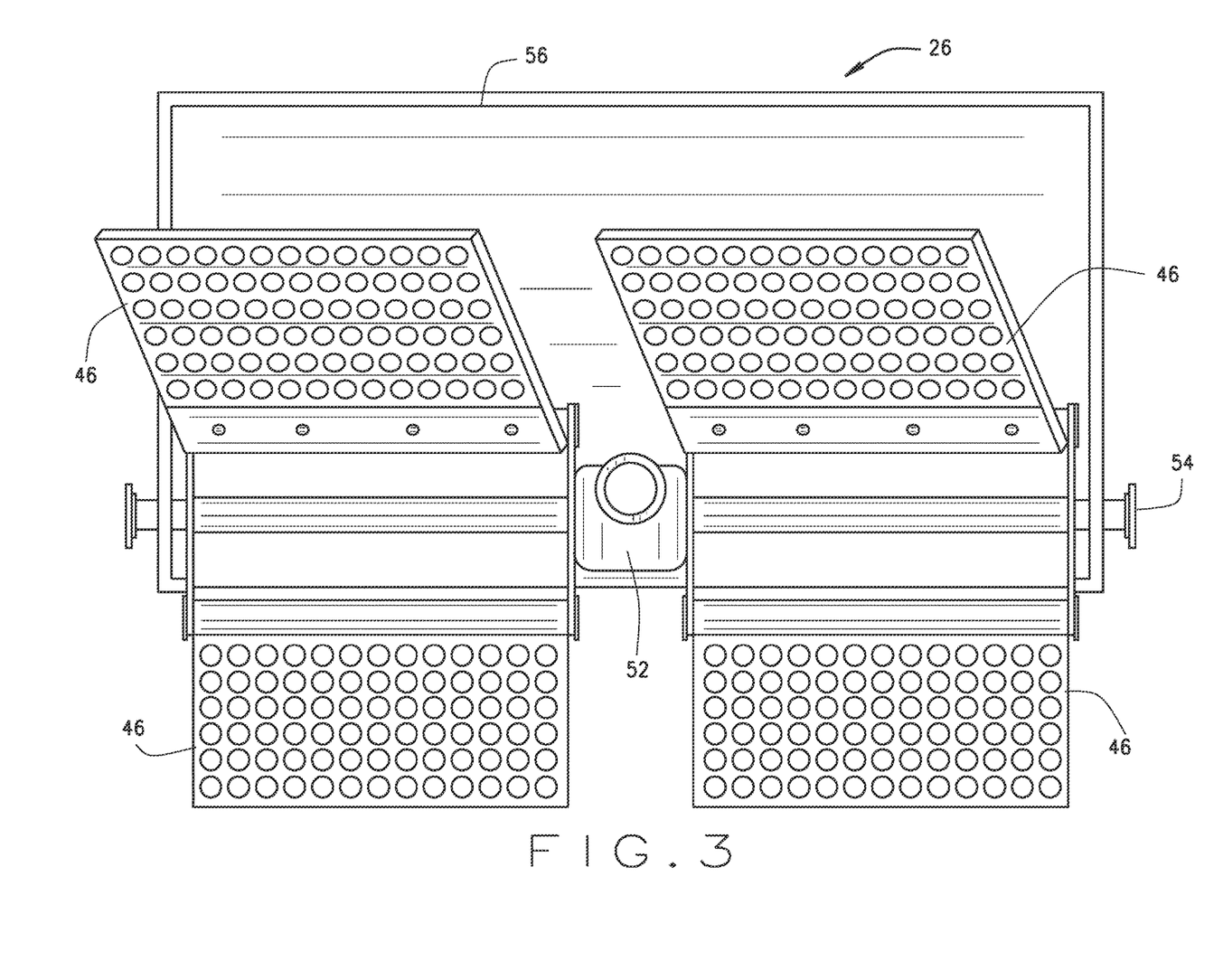
FIG. 3 is a front view of the plant engaging head of the mobile seed pod shatter test system shown in FIGS. 1 and 2, exemplarily illustrating rotating plant contact implements of the system shown in FIGS. 1 and 2, in accordance with various embodiments of the present disclosure.
Figure 6:
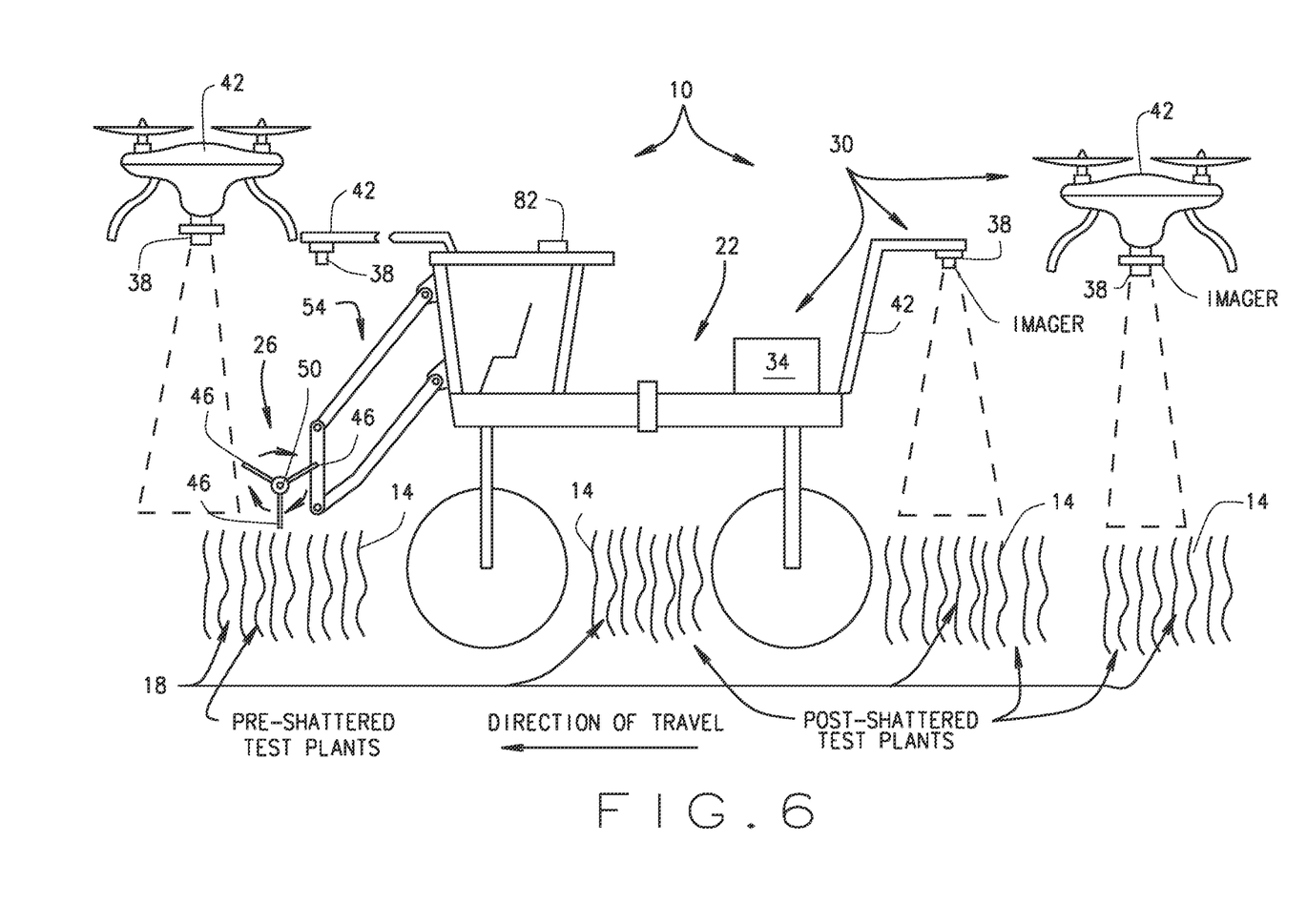
FIG. 6 is side view of the mobile seed pod shatter test system shown in FIGS. 1, 2, 3, 4 and 5 exemplarily illustrating the system including a plurality of imagers, in accordance with various embodiments of the present disclosure.

Referring now to FIGS. 1 and 6, as described above, the shatter test system 10 is structured and operable to: 1) capture various image data of the plants 14, via the imager(s) 38, at least subsequent to being operated on by the plant engaging head(s) 26, and in some instances prior to and subsequent to being operated on by the plant engaging head(s) 26; and 2) analyze the captured data, via execution of the plant analytics software, to determine the amount of pod shattering caused in the plants 14 by the shatter test system 10. Whereafter, the pod shatter data and information can be utilized to determine whether the one or more of the plants 14 should be used as a parent in future commercial plant products. As also described above, the plant imager(s) 38 can be mounted to the mobile platform 22 and/or to a separate imager carrier 42. For example, as exemplarily illustrated in FIGS. 1 and 6 one or more imager 38 can be mounted to the mobile platform 22 and any location and any connection means such as the image carrier(s) 42. Additionally, or alternatively, one or more imager can be mounted to a device that is separate from the mobile platform 22 such as one or more UAVs as exemplarily illustrated in FIGS. 1 and 6, or one or more separate terrestrial vehicles, such as terrestrial robotic device. Accordingly, the imagers 38 can capture image data of the plants 14 after, or before and after, the plants 14 have been conditioned by the plant engaging head(s) 26 and transmit or communicate the captured image data to the data processing system 34. Thereafter, the data processing system 34, via execution of the plant analytics software, can generate and compile various types phenotypic and/or genotypic information about the conditioned plants 14, such as an amount and/or percentage of shatter seed pods are present on the conditioned plants 14. Subsequently, the data and information generated and compiled by the data processing system can be utilized to make decisions in a plant breeding pipeline, for example, should the plants 14 in a particular test plot 18 be used as parent plants in the breeding of future commercial plant products. Additionally, it is envisioned that the data processing system 34, via execution of the plant analytics software, can generate and compile various types plant health data, disease detection data and identification, pest infestation data and identification The imager(s) 38 can comprise any type of imaging device, sensor, (hyperspectral) camera, charged coupled device (CCD) camera, an infrared (IR) camera, a high resolution digital camera, LiDAR, time-of-flight camera, or any other suitable imaging device that is useful for collecting image data and/or other energy values (e.g. digital images, IR images, intensities of electromagnetic energy at certain wavelengths, etc.). In various embodiments, the shatter test system 10 can comprise a global positioning system (GPS) transceiver 82 that is communicatively connected (wired or wirelessly) to the data processing system 34. In such instances, the image data captured by the imager(s) 38 can be geospatially tagged as the shatter test system 10 is moved through the test plot 18, thereby providing precise locations of each plant 14 or group of plants 14 in a test plot 18, or a test plot 18 in a field of many test plots 18 and a respective pod shatter resistance score (described below) of the plants 14.

In various embodiments, the amount of seed pod shattering produced by the shatter test system 10 (along with other variables known to affect shattering, such as operating conditions, climate, soil conditions, plant types, etc.) can be quantified and compared to generate a reliable and objective method of scoring the resulting seed pod shattering under different operating conditions, climate, soil conditions, plant types, etc., which can be used to select and/or breed plants for improved and/or otherwise desired seed pod shattering characteristics.

Additionally, in various embodiments, the plant analytics software can include machine-learning, or artificial intelligence (AI) algorithms that are trained to analyze the image data captured and score the shatter resistance of the plants 14 based on the severity of seed pod shattering exhibited in the images (e.g. by comparing the amount of seed pod shattering in the plants 14 before conditioning by the shatter test system 10 to the amount of seed pod shattering in the images of the plants 14 captured after conditioning by the shatter test system 10). In such embodiments, over time, the image data analysis and scoring, thereby improving the accuracy and efficiency of the shatter test system 10 at collecting data and improving plant breeding decision to make better plants. Alternatively, in various embodiments, the width of the plant engaging head 26, and hence the width of that of the swath of plants 14 that the plant contact implements 46 contact and condition, can be less that the respective plot width. In such embodiments, it is envisioned that image data can be simultaneously collected from the conditioned plants 14 and the adjacent non-conditioned plants 14. Therefore, in such embodiments, the need to acquire image data of the plants 14 before the plants 14 in a plot are conditioned and subsequently acquire image data after the respective plants 14 have been conditioned by the system 10 image can be eliminated. In such instances, a side-by-side comparison of conditioned and non-conditioned plants 14 can be done as the system 10 traverse the respective plot.

In various embodiments, it is envisioned that the plant analytics software can be trained to recognize and score pod shattering resistance faster and more accurately using methods known in the art related to electronic image recognition. The imaging analysis and scoring can be done simultaneously as the images are collected and/or while the field is being subjected to these pod shattering methods, or the analysis and scoring could be done subsequent to operation of the shatter test system 10 and the conditioning of the plants 14.

For example, in the embodiments wherein image data of the plants 14 in a test plot 18 is collected before and after conditioning by the shatter test system 10, it is envisioned that the AI plant analytics software can compare the image data collected before conditioning to the image data collected after conditioning. Then based on the comparison, and in various instances one or more other visual metric, determine an amount and/or percentage of seed pod shattering resulting from the conditioning. The amount and/or percentage of seed pod shattering can then be converted to a pod shatter resistance score or value that can be used to give a numeric value to the seed pod shattering resistance of the particular type (e.g., hybrid) of plants 14 in the respective test plot 18.

The ability to automatically raise and lower in real time the plant engaging head(s) 26 (as described above) combined with the ability to adjust the rotational speed of the plant contact implement(s) 46 in real time (as described above) allow the shatter test system 10 to produce repeatable results across different crop conditions such as operating conditions, climate, soil conditions, plant types, variances in canopy height, etc. Moreover, based on the premise that a consistent contact force of the contact implement(s) 46 and a consistent engagement height of the plant engaging head (s) 26 relative to the canola of the plants being conditioned by the shatter test system 10 will produce different seed pod shattering results between different hybrids of plants 14 having varying seed pod shatter resistance, the ability to control the operational variables of the shatter test system is important. A proposed relationship between the operational variables and a given hybrid's seed pod shatter resistance (SRH) is as follows:

$$SRH = a\omega + bV \times cd \tag{1}$$

wherein $\omega$=rotational velocity=linear velocity of the plant contact implement(s) divided by the radius of the plant contact implements; V=velocity of the shatter test system (e.g., the mobile platform); d=depth of engagement of the plant contact implement(s) into the canopy; and wherein a, b, c are the coefficients for the respective variables.

Figure 8:
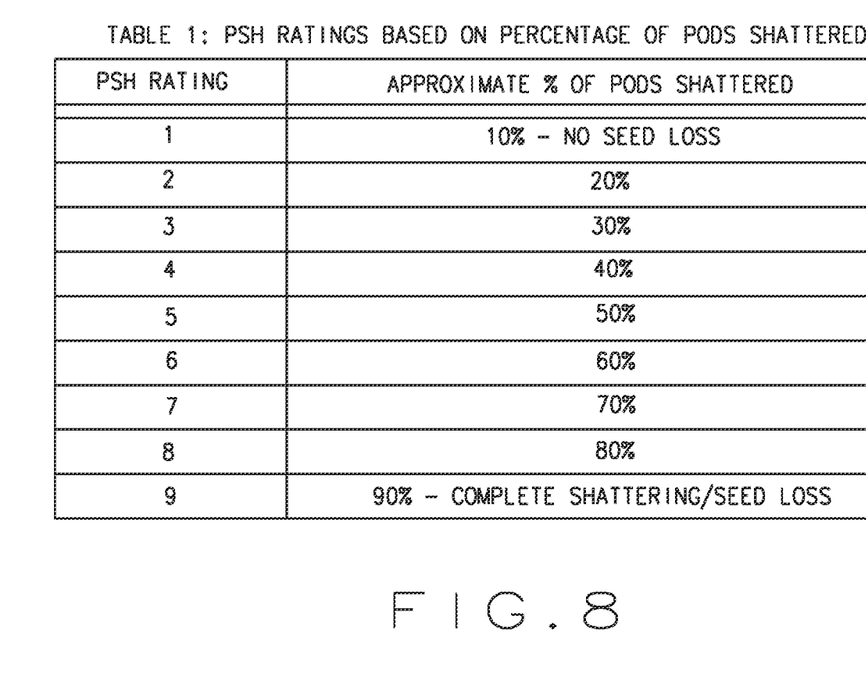
FIG. 8 is exemplary illustration of shatter resistance scoring (or rating) table used to score the shatter resistance of plants, in accordance with various embodiments of the present disclosure.

Hybrids with a higher seed pod shatter resistance values will require greater values of the equation variables to induce seed pod shattering, and conversely for lower seed pod shatter resistant hybrids. By adjusting the variables to the point that the most seed pod shatter resistant hybrids just begin to shatter, it will be possible to create a relative seed pod shatter resistance score, or rating, based upon how much seed pod shattering of a particular hybrid results from conditioning by the shatter test system 10 relative to the most seed pod shattering resistant hybrids for a constant setting of variables. An exemplary shatter resistance scoring (or rating) table is shown as Table 1 in FIG. 8, wherein PSH stands for "pod shattering".

Figure 7:
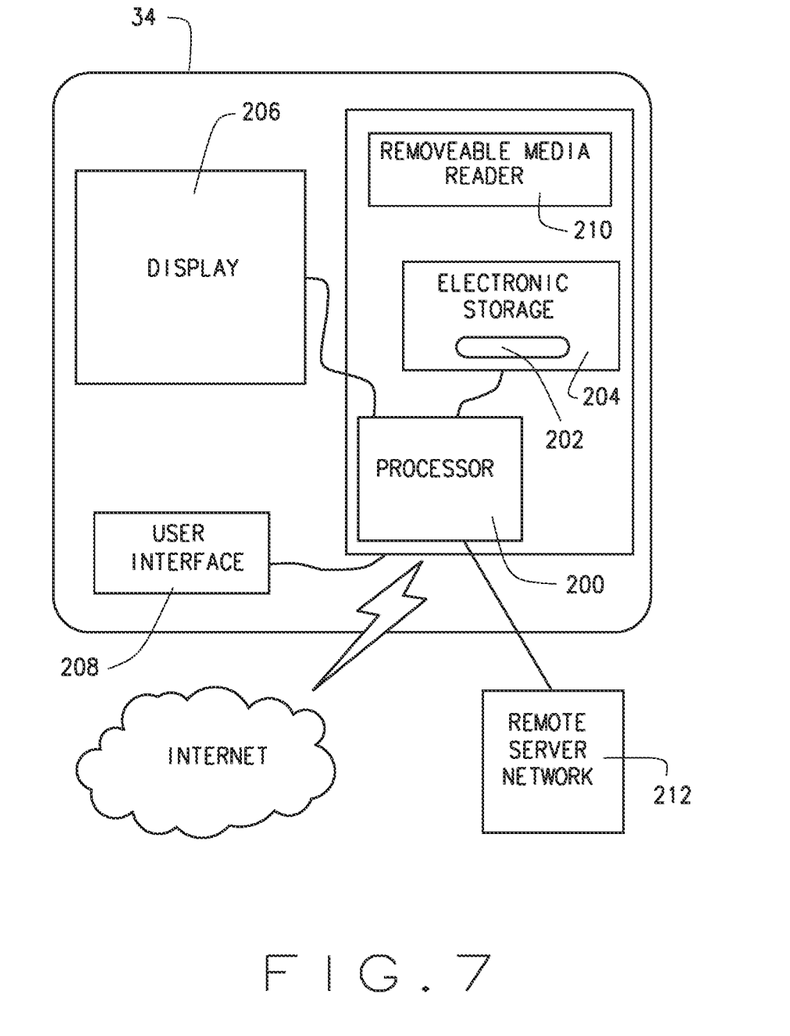
FIG. 7 is a block diagram of a data processing system of the mobile seed pod shatter test system shown in FIGS. 1, 2, 3, 4, 5 and 6, in accordance with various embodiments of the present disclosure.

Referring now to FIG. 7, as described above, the data processing system 34 is structured and operable to control one or more automated operations of the mobile shatter test system 10. For example, in various embodiments, the data processing system 34 can entirely control or control in part, via communication with other control devices of the system 10, the automated operations of the lift assembly 54 and the plant engaging head(s) 26. More particularly, the data processing system 34 is a computer-based system that includes one or more computers, controllers, programmable circuitry, electrical modules, etc. that can be located at various locations of the system 10. In various embodiments, the data processing system 34 comprises one or more processor 200 structured and operable to execute the plant analytics software, which can include one or more programs, algorithms, and/or code (exemplarily illustrated in FIG. 10 as plant analytics software 202), whereby operations of the lift assembly 54 and the plant engaging head(s) 26, and various other features, functions, systems, devices, assemblies, etc., of the system 10 can be controlled.

In various implementations, the data processing system 34 additionally includes at least one electronic storage device 204 that comprises a computer readable medium, e.g., non-transitory, tangible, computer readable medium, such as a hard drive, erasable programmable read-only memory (EPROM), electronically erasable programmable read-only memory (EEPROM), read-write memory (RWM), etc. Other, non-limiting examples of the non-transitory, tangible, computer readable medium are nonvolatile memory, magnetic storage, and optical storage. Generally, the computer readable memory can be any electronic data storage device for storing such things as the various software, programs, algorithms, code, digital information, data, look-up tables, spreadsheets and/or databases, etc., used and executed during operation the system 10, as described herein. Furthermore, in various implementations, the data processing system 34 can include at least one display 206 for displaying such things as information, data and/or graphical representations, and at least one user interface device 208 such as a keyboard, mouse, stylus, and/or an interactive touch-screen on the display 206. The user interface 208 is structured and operable to allow a user of the system 10 to input control data and information and retrieve operation status data and information regarding the operation of the system 10.

Still further, in various implementations, the data processing system 34 can include a removable media reader 210 for reading information and data from and/or writing information and data to removable electronic storage media such as floppy disks, compact disks, DVD disks, zip disks, flash drives or any other computer readable removable and portable electronic storage media. In various embodiments the removable media reader 210 can be an I/O port utilized to read external or peripheral memory devices such as flash drives or external hard drives. Further yet, in various implementations, data processing system 34 can be communicatively connectable to a remote server network 212, e.g., a local area network (LAN) or a wide area network (WAN), via a wired or wireless link. Accordingly, the data processing system 34 can communicate with the remote server network 212 to upload and/or download data, information, algorithms, software programs, and/or receive operational commands. Additionally, in various implementations, data processing system 34 can be structured and operable to access the Internet to upload and/or download data, information, algorithms, software programs, etc., to and from Internet sites and network servers. In various embodiments, the various software, programs, algorithms, and/or code executed by the processor(s) 200 to control the operations of the system 10 can be top-level system control software that not only controls the discrete hardware functionality of the system 10, but also prompts an operator for various inputs. Various other embodiments can utilize relay logic.

The description herein is merely exemplary in nature and, thus, variations that do not depart from the gist of that which is described are intended to be within the scope of the teachings. Moreover, although the foregoing descriptions and the associated drawings describe example embodiments in the context of certain example combinations of elements and/or functions, it should be appreciated that different combinations of elements and/or functions can be provided by alternative embodiments without departing from the scope of the disclosure. Such variations and alternative combinations of elements and/or functions are not to be regarded as a departure from the spirit and scope of the teachings.

What is claimed is:

1. A seed pod shatter test system for determining the resistance to seed pod shattering in various plants, said system comprising:
    a mobile platform structured and operable to traverse at least one row of plants growing in plot;
    at least one plant engaging head mounted to a front of the mobile platform, the at least one plant engaging head structured and operable to condition each of the plurality of plants in the at least one row of plants growing in the plot by contacting each of the plurality of plants in the at least one row of plants growing in the plot in the at least one row with a predetermined amount of force to simulate exposure of the plurality of plants in the at least one row of plants growing in the plot to environmental weather conditions and elements as the mobile platform traverses the at least one row of plants growing in the plot; and
    a data collections and analysis system structured and operable to determine an amount of seed pod shattering that occurred in the plurality of plants in the at least one row of plants growing in the plot as a result of the contact by the at least one plant engaging head.

2. The system of claim 1, wherein the at least one plant engaging head comprises:
    a housing;
    a barrel rotationally mounted within the housing;
    a motor operationally connected to the barrel and structured and operable to controllably rotate the barrel about a longitudinal axis of the barrel; and
    at least one plant contact implement mounted to the barrel and structured and operable to condition the plurality of plants in the at least one row of plants growing in the plot by contacting the plurality of plants in the at least one row of plants growing in the plot with the predetermined amount of force as result of the controlled rotation of the barrel and the traversing of the row or plants by the mobile platform.

3. The system of claim 2, wherein the data collections and analysis system comprises:
- at least one imager mounted to at least one of the mobile platform and an imager carrier that is separate from the mobile platform, the at least one imager structured and operable to capture image data of the plurality of plants in the at least one row of plants growing in the plot at least one of:
  - subsequent to being conditioned by the at least one plant engaging head; and
  - before and subsequent to being conditioned by the at least one plant engaging head;
- a data processing system communicatively connected to the at least one imager and structured and operable to:
  - receive the captured image data from the at least one imager;
  - determine an amount of seed pod shattering that occurred in the plurality of plants in the at least one row of plants growing in the plot as a result of the conditioning by the at least one plant engaging head; and
  - determine a seed pod resistance score for the plurality of plants in the at least one row of plants growing in the plot based on the determined amount of seed pod shattering.

4. The system of claim 1 further comprising a lift assembly mounted to the mobile platform and to which the at least one plant engaging head is mounted, the lift assembly structured and operable to position the at least one plant engaging head at a desired height relative to a top of a canopy of the plurality of plants in the at least one row of plants growing in the plot.

5. The system of claim 4, wherein the lift assembly comprises an automated actuator communicatively connected to the data collections and analysis system and structured and operable to automatically position in real time the at least one plant engaging head at a desired height relative to a top of one or more of the plants in the at least one row of plants growing in the plot as the mobile platform traverses the at least one row of plants in the at least one row of plants growing in the plot.

6. The system of claim 5 further comprising a sensor bar assembly disposed in front of the at least one plant engaging head, and structured and operable to detect, and communicate to the data collections and analysis system, the top of one or more of the plants in the at least one row of plants growing in the plot as the mobile platform traverses the at least one row of plants in the at least one row of plants growing in the plot.

7. The system of claim 6, wherein the sensor bar assembly comprising:
- a sensor bar; and
- a sensor system connected to the sensor bar and communicatively connected to the data collections and analysis system, the sensor system structured and operable to detect the presence of a plant within a sensing field of the sensor system, and to detect the top of one or more of the plants in the at least one row of plants growing in the plot as the mobile platform traverses the at least one row of plants in the at least one row of plants growing in the plot.

8. The system of claim 7, wherein the sensor system comprises:
- at least one transceiver connected at a first end of the sensor bar; and
- at least one reflector connected at a second end of the sensor bar, and the sensing field is a line-of-sight between the at least one transceiver and the reflector.

9. A seed pod shatter test system for determining the resistance to seed pod shattering in various plants, said system comprising:
- a mobile platform structured and operable to traverse at least one row of plants growing in plot;
- at least one plant engaging head mounted to a front of the mobile platform, the at least one plant engaging head structured and operable to condition each of the plurality of plants in the at least one row of plants growing in the plot by contacting each of the plurality of plants in the at least one row of plants growing in the plot in the at least one row with a predetermined amount of force to simulate exposure of the plurality of plants in the at least one row of plants growing in the plot to environmental weather conditions and elements as the mobile platform traverses the at least one row of plants growing in the plot, the at least one plant engaging head comprises:
  - a housing;
  - a barrel rotationally mounted within the housing;
  - a motor operationally connected to the barrel and structured and operable to controllably rotate the barrel about a longitudinal axis of the barrel; and
  - at least one plant contact implement mounted to the barrel and structured and operable to condition the plants by contacting the plants with the predetermined amount of force as result of the controlled rotation of the barrel and the traversing of the row or plants by the mobile platform; and
- a data collections and analysis system structured and operable to determine an amount of seed pod shattering that occurred in the plurality of plants in the at least one row of plants growing in the plot as a result of the contact by the at least one plant engaging head.

10. The system of claim 9, wherein the data collections and analysis system comprises:
- at least one imager mounted to at least one of the mobile platform and an imager carrier that is separate from the mobile platform, the at least one imager structured and operable to capture image data of the plurality of plants in the at least one row of plants growing in the plot at least one of:
  - subsequent to being conditioned by the at least one plant engaging head; and
  - before and subsequent to being conditioned by the at least one plant engaging head;
- a data processing system communicatively connected to the at least one imager and structured and operable to:
  - receive the captured image data from the at least one imager;
  - determine an amount of seed pod shattering that occurred in the plurality of plants in the at least one row of plants growing in the plot as a result of the conditioning by the at least one plant engaging head; and
  - determine a seed pod resistance score for the plants in the at least one row of plants growing in the plot based on the determined amount of seed pod shattering.

11. The system of claim 9 further comprising a lift assembly mounted to the mobile platform and to which the at least one plant engaging head is mounted, the lift assembly structured and operable to position the at least one plant engaging head at a desired height relative to a top of a canopy of the plants in the at least one row of plants growing in the plot.

12. The system of claim 11, wherein the lift assembly comprises an automated actuator communicatively connected to the data collections and analysis system and structured and operable to automatically position in real time the at least one plant engaging head at a desired height relative to a top of one or more of the plants in the at least one row of plants growing in the plot as the mobile platform traverses the at least one row of plants in the at least one row of plants growing in the plot.

13. The system of claim 12 further comprising a sensor bar assembly disposed in front of the at least one plant engaging head, and structured and operable to detect, and communicate to the data collections and analysis system, the top of one or more of the plants in the at least one row of plants growing in the plot as the mobile platform traverses the at least one row of plants growing in the plot.

14. The system of claim 13, wherein the sensor bar assembly comprising:
    a sensor bar; and
    a sensor system connected to the sensor bar and communicatively connected to the data collections and analysis system, the sensor system structured and operable to detect the presence of a plant within a sensing field of the sensor system, and to detect the top of one or more of the plants in the at least one row of plants growing in the plot as the mobile platform traverses the at least one row of plants growing in the plot.

15. A method for determining the resistance to seed pod shattering in various plants, said method comprising:
    traversing at least one row of a plurality of plants growing in plot utilizing a mobile platform of a seed pod shatter test system;
    conditioning each of the plurality of plants in the at least one row of plants growing in the plot by contacting each of the plurality of plants in the at least one row of plants growing in the plot with a predetermined amount of force to simulate exposure of the plurality of plants in the at least one row of plants growing in the plot to environmental weather conditions and elements as the mobile platform traverses the at least one row of plants growing in the plot utilizing at least one plant engaging head mounted to a front of the mobile platform of the seed pod shatter test system, wherein the at least one plant engaging head comprises:
        a housing;
        a barrel rotationally mounted within the housing;
        a motor operationally connected to the barrel and structured and operable to controllably rotate the barrel about a longitudinal axis of the barrel; and
        at least one plant contact implement mounted to the barrel and structured and operable to condition the plurality of plants in the at least one row of plants growing in the plot by contacting the plurality of plants in the at least one row of plants growing in the plot with the predetermined amount of force as result of the controlled rotation of the barrel and the traversing of the at least one row or plants growing in the plot by the mobile platform; and
    determining an amount of seed pod shattering that occurred in the plurality of plants in the at least one row of plants growing in the plot as a result of the contact by the at least one plant engaging head utilizing a data collections and analysis system of the seed pod shatter test system.

16. The method of claim 15, wherein determining the amount of seed pod shattering comprises:
    capturing image data of the plurality of plants in the at least one row of plants growing in the plot, utilizing at least one imager of the seed pod shatter test system mounted to at least one of the mobile platform and an imager carrier carries that is separate from the mobile platform, the image data captured at least one of:
        subsequent to being conditioned by the at least one plant engaging head; and
        before and subsequent to being conditioned by the at least one plant engaging head;
    determining an amount of seed pod shattering that occurred in the plurality of plants in the at least one row of plants growing in the plot as a result of the conditioning by the at least one plant engaging head, utilizing a data collection and analysis system of the seed pod shatter test system communicatively connected to the at least one imager; and
    determining a seed pod resistance score for the plurality of plants in the at least one row of plants growing in the plot based on the determined amount of seed pod shattering utilizing the data collection and analysis system.

17. The method of claim 16 further comprising positioning the at least one plant engaging head at a desired height relative to a top of a canopy of the plurality of plants in the at least one row of plants growing in the plot utilizing a lift assembly mounted to the mobile platform and to which the at least one plant engaging head is mounted.

18. The method of claim 17, wherein positioning the at least one plant engaging head comprises automatically positioning in real time the at least one plant engaging head at a desired height relative to a top of one or more of the plants in the at least one row of plants growing in the plot as the mobile platform traverses the at least one row of plants growing in the plot utilizing an automated actuator of the lift assembly communicatively connected to the data collections and analysis system.

19. The method of claim 18, wherein automatically positioning in real time the at least one plant engaging head comprises detecting, and communicating to the data collections and analysis system, the top of one or more of the plants in the at least one row of plants growing in the plot as the mobile platform traverses the at least one row of plants growing in the plot, utilizing a sensor bar assembly of the seed pod shatter test system that is disposed in front of the at least one plant engaging head.

20. The method of claim 19, wherein detecting, and communicating to the data collections and analysis system, comprises;
    detecting the presence of a plant within a sensing field of a sensor system of a sensor bar assembly of the seed pod shatter test system; and
    detecting the top of one or more of the plants in the at least one row of plants growing in the plot as the mobile platform traverses the at least one row of plants growing in the plot, utilizing the sensor bar assembly.

* * * * *